(12) United States Patent
Holland et al.

(10) Patent No.: US 11,602,271 B2
(45) Date of Patent: Mar. 14, 2023

(54) COMMON PATH WAVEGUIDES FOR STABLE OPTICAL COHERENCE TOMOGRAPHY IMAGING

(71) Applicant: Novartis AG, Basel (CH)

(72) Inventors: Guy Holland, San Juan Capistrano, CA (US); Muhammad K Al-Qaisi, Ladera Ranch, CA (US)

(73) Assignee: Alcon Inc., Fribourg (CH)

( * ) Notice: Subject to any disclaimer, the term of this patent is extended or adjusted under 35 U.S.C. 154(b) by 1054 days.

(21) Appl. No.: 16/284,025

(22) Filed: Feb. 25, 2019

(65) Prior Publication Data

US 2019/0269320 A1 Sep. 5, 2019

Related U.S. Application Data

(60) Provisional application No. 62/637,194, filed on Mar. 1, 2018.

(51) Int. Cl.
| | |
|---|---|
| *A61B 3/10* | (2006.01) |
| *A61F 9/008* | (2006.01) |
| *G02B 6/02* | (2006.01) |
| *G01B 9/02091* | (2022.01) |
| *A61B 5/00* | (2006.01) |
| *G01B 9/02056* | (2022.01) |

(52) U.S. Cl.
CPC ............ *A61B 3/102* (2013.01); *A61B 5/0066* (2013.01); *A61F 9/008* (2013.01); *G01B 9/02057* (2013.01); *G01B 9/02091* (2013.01); *G02B 6/02395* (2013.01); *A61B 2560/0223* (2013.01); *A61F 2009/00851* (2013.01)

(58) Field of Classification Search
CPC .................. A61B 3/102; A61B 5/0066; A61B 2560/0223; A61F 9/008; A61F 2009/00851; G01B 9/02057; G01B 9/02091; G02B 6/02395
USPC .......................................................... 600/425
See application file for complete search history.

(56) References Cited

U.S. PATENT DOCUMENTS

| | | | |
|---|---|---|---|
| 2007/0081166 A1* | 4/2007 | Brown | G01B 9/02089 356/497 |
| 2008/0049232 A1* | 2/2008 | Vakoc | A61B 3/1225 356/477 |

(Continued)

FOREIGN PATENT DOCUMENTS

| | | |
|---|---|---|
| AR | 097650 A1 | 4/2016 |
| CN | 101406391 A | 4/2009 |

(Continued)

*Primary Examiner* — William R Alexander
*Assistant Examiner* — Rahman Abdur

(57) ABSTRACT

An OCT imaging system may include an OCT light source operable to emit an OCT light beam, and a beam splitter operable to split the OCT light beam into a sample beam, transferred to a sample arm waveguide, and a reference beam, transferred to a reference arm waveguide. The sample arm waveguide and the reference arm waveguide may be coupled together within a cladding, wherein the cladding improves a calibration of a generated OCT image by fixing axial movement of the sample arm and reference arm waveguides relative to one another. By routing long reference and sample arm waveguide fibers together in the OCT system using a sheath/cladding, OCT image offset due to asymmetrical fiber stretching can be minimized or eliminated.

12 Claims, 5 Drawing Sheets

(56) References Cited

U.S. PATENT DOCUMENTS

| | | |
|---|---|---|
| 2012/0226150 A1 | 9/2012 | Balicki |
| 2014/0219613 A1* | 8/2014 | Nielson ................ G02B 6/4471 |
| | | 385/78 |
| 2014/0293225 A1 | 10/2014 | Parto |
| 2017/0131157 A1 | 5/2017 | Galstian |
| 2018/0008143 A1 | 1/2018 | Chong |

FOREIGN PATENT DOCUMENTS

| | | |
|---|---|---|
| CN | 101849816 A | 10/2010 |
| CN | 102046067 A | 5/2011 |
| CN | 102122045 A | 7/2011 |
| CN | 102641116 A | 8/2012 |
| CN | 102783937 A | 11/2012 |
| CN | 102824161 A | 12/2012 |
| CN | 104545788 A | 4/2015 |
| CN | 104781651 A | 7/2015 |
| CN | 105271704 A | 1/2016 |
| CN | 204989532 U | 1/2016 |
| CN | 205083436 U | 3/2016 |
| CN | 106645080 A | 5/2017 |
| CN | 106691364 A | 5/2017 |
| CN | 206274472 U | 6/2017 |
| CN | 107427385 A | 12/2017 |
| EP | 1928297 A1 | 6/2008 |
| JP | 2002143088 A | 5/2002 |

* cited by examiner

COMMON PATH WAVEGUIDES FOR STABLE OPTICAL COHERENCE TOMOGRAPHY IMAGING

FIELD

The present disclosure is directed to Optical Coherence Tomography (OCT) imaging systems, and more particularly, to reducing differential fiber stretching between two fiber cores in OCT imaging systems.

BACKGROUND

The fields of microsurgical and ophthalmic surgical procedures are evolving rapidly. Many of these procedures now involve the use of imaging probes. These imaging probes can involve fiber-based video imaging, OCT imaging, and OCT-imaging based computerized operations. To image with high quality and depth resolution, the imaging systems and their imaging depths are to be calibrated with high precision. Precisely calibrated imaging systems can provide accurate images of the tissue being treated or diagnosed with good depth-calibration and good resolution.

In some conventional OCT systems, optical fibers may be used for reference and sample arms. During an OCT procedure, the reference and/or sample arm waveguide fibers may become stretched, causing the resulting reconstructed OCT image to be offset relative to the initial calibrated position. As a result, it is often necessary to recalibrate the positions of the reference and sample arms. It is with respect to at least this deficiency of conventional OCT systems that the present disclosure is provided.

SUMMARY

One or more embodiments of the present disclosure include an Optical Coherence Tomography (OCT) imaging system having an OCT light source operable to emit an OCT light beam, and a beam splitter operable to split the OCT light beam into a sample beam, transferred to a sample arm waveguide, and a reference beam, transferred to a reference arm waveguide. The sample arm waveguide and the reference arm waveguide may be coupled together within a cladding, wherein the cladding improves a calibration of a generated OCT image by fixing axial movement of the sample arm and reference arm waveguides relative to one another.

One or more embodiments of the present disclosure include an Optical Coherence Tomography (OCT) fiber assembly having a sample arm waveguide receiving a sample beam, a reference arm waveguide receiving a reference beam, and a cladding coupling the sample arm waveguide and the reference arm waveguide together. The cladding improves a calibration of a generated OCT image by minimizing axial movement of the sample arm and reference arm waveguides relative to one another.

One or more embodiments of the present disclosure include an Optical Coherence Tomography (OCT) imaging system, having an OCT light source operable to emit an OCT light beam, and a beam splitter operable to split the OCT light beam into a sample beam delivered to a sample arm waveguide, and a reference beam delivered to a reference arm waveguide. The OCT imaging system may further include a cladding coupling the sample arm waveguide and the reference arm waveguide together, wherein the cladding is conformally disposed over the sample arm waveguide and the reference arm waveguide and improves a calibration of a generated OCT image by minimizing axial movement of the sample arm and reference arm waveguides relative to one another.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

Figure 1:
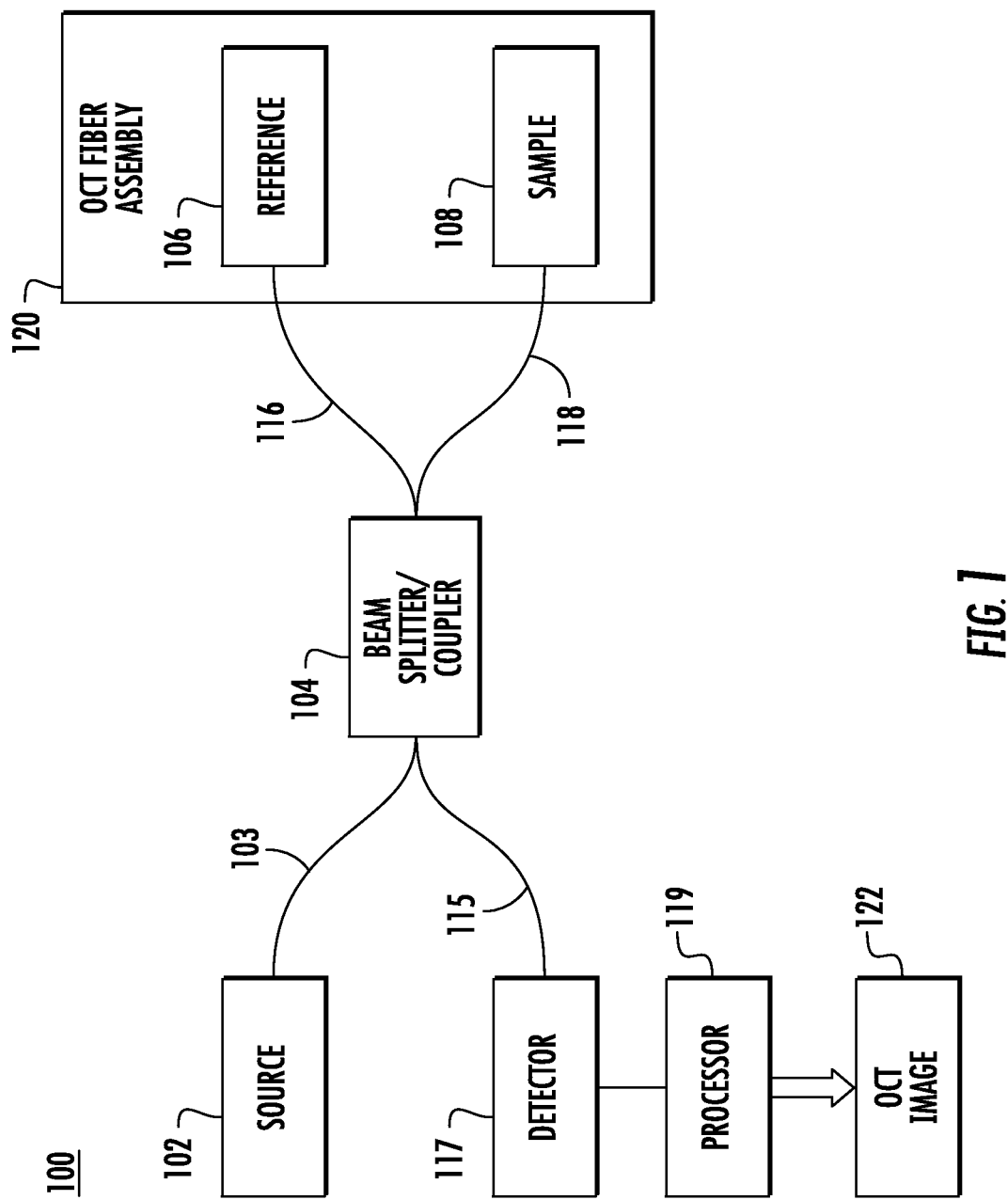
FIG. 1 illustrates a block diagram of an example OCT system according to aspects of the present disclosure.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended unless specifically indicated. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For simplicity, in some instances the same reference numbers are used throughout the drawings to refer to the same or like parts.

The present disclosure is broadly directed to systems and apparatuses for diagnosing and/or treating an eye of a patient. More specifically, provided herein are Optical Coherence Tomography (OCT) imaging systems and OCT fiber assemblies. In one embodiment, an OCT imaging system may include an OCT light source operable to emit an OCT light beam, and a beam splitter operable to split the OCT light beam into a sample beam, transferred to a sample arm waveguide, and a reference beam, transferred to a reference arm waveguide. The sample arm waveguide and the reference arm waveguide may be coupled together within a cladding, wherein the cladding improves a calibration of a generated OCT image by fixing axial movement of the sample arm and reference arm waveguides relative to one another. By routing long reference and sample arm waveguide fibers together in the OCT system using a sheath/cladding, OCT image offset due to asymmetrical fiber stretching can be minimized or eliminated.

Embodiments herein provide an advantage over existing common-path OCT approaches in which both sample and reference beams are carried on one fiber core, and the reference signal is generated as the reflection from the fiber tip. Existing approaches are limited by reference arm waveguide optical power, as well as a fixed path length mismatch between the reference arm waveguide and the sample arm. Embodiments herein provide a solution to these limitations, as well as others, by decoupling the optical paths while keeping the optical paths in a common physical path.

FIG. 1 illustrates an OCT imaging system 100 consistent with some embodiments of the present disclosure. OCT is an optical imaging approach that is capable of imaging targets in a range of depths and organizing these in-depth images into two or three-dimensional images with micron-resolution. The possible targets include biological tissues, including the human eye. OCT imaging system 100 can include an OCT light source or laser source 102, configured to emit an OCT light beam 103 to a beam splitter/coupler 104. In some embodiments, the light source 102 can emit a coherent light with a defined spectrum designed according to the requirements of the OCT imaging technique. In some embodiments, the OCT light source 102 can include a superluminescent diode (SLD), a white light source with a sufficiently broad bandwidth, a swept laser, configured to sweep a sufficiently wide bandwidth, or a comb laser with discrete wavelengths. The beam splitter 104 can split the OCT light beam 103 into a sample beam 118, transferred to a sample arm waveguide 108, and a reference beam 116, transferred to a reference arm waveguide 106. The sample beam 118 can be guided and projected by a probe 110 (FIG. 2) onto a target, from where it can be returned as a returned sample beam. The reference beam 116 can be guided by the reference arm waveguide 106 to a reference that can return it as a returned reference beam. As will be described in greater detail below, the sample arm waveguide 108 and the reference arm waveguide 106 may be part of an OCT fiber assembly 120 including a cladding (not shown in FIG. 1) for coupling together the sample arm waveguide 108 and the reference arm waveguide 106 to minimize axial movement (e.g., stretching or shifting) of one arm relative to the other.

The beam splitter/coupler 104 can combine the returned sample beam and the returned reference beam into an interference beam 115. An imaging detector 117 can detect the interference beam 115 and an imaging processor 119 can generate an OCT image 122 from the detected interference beam 115. According to the principles of operation, the OCT imaging system 100 uses the returned reference beam returned from a working distance or depth within the target having the same optical path length as the returned reference beam. Therefore, adjusting the length and/or position of the reference arm waveguide 106 to select the intended imaging depth or working distance may be used to calibrate the OCT imaging system 100.

In some embodiments, the imaging detector 117 may be a spectrometer with a detector array in a spectrometer based Fourier-Domain OCT imaging system 100, or a photodiode detector in a swept-source Fourier-domain OCT imaging system 100. Consistent with some embodiments of the disclosure, the imaging processor 119 may include one or more computing systems including computer-readable media storing instructions for image recognition and processing. The instructions can be executed by one or more processors of the computing systems to process the interference beam 115 detected by imaging detector 117. The imaging processor 119 may also be a microcontroller, application-specific integrated circuit (ASIC), or other programmable device. According to some embodiments of the present disclosure, the target may correspond to a tissue in an eye, which may be a human eye.

Figure 2:
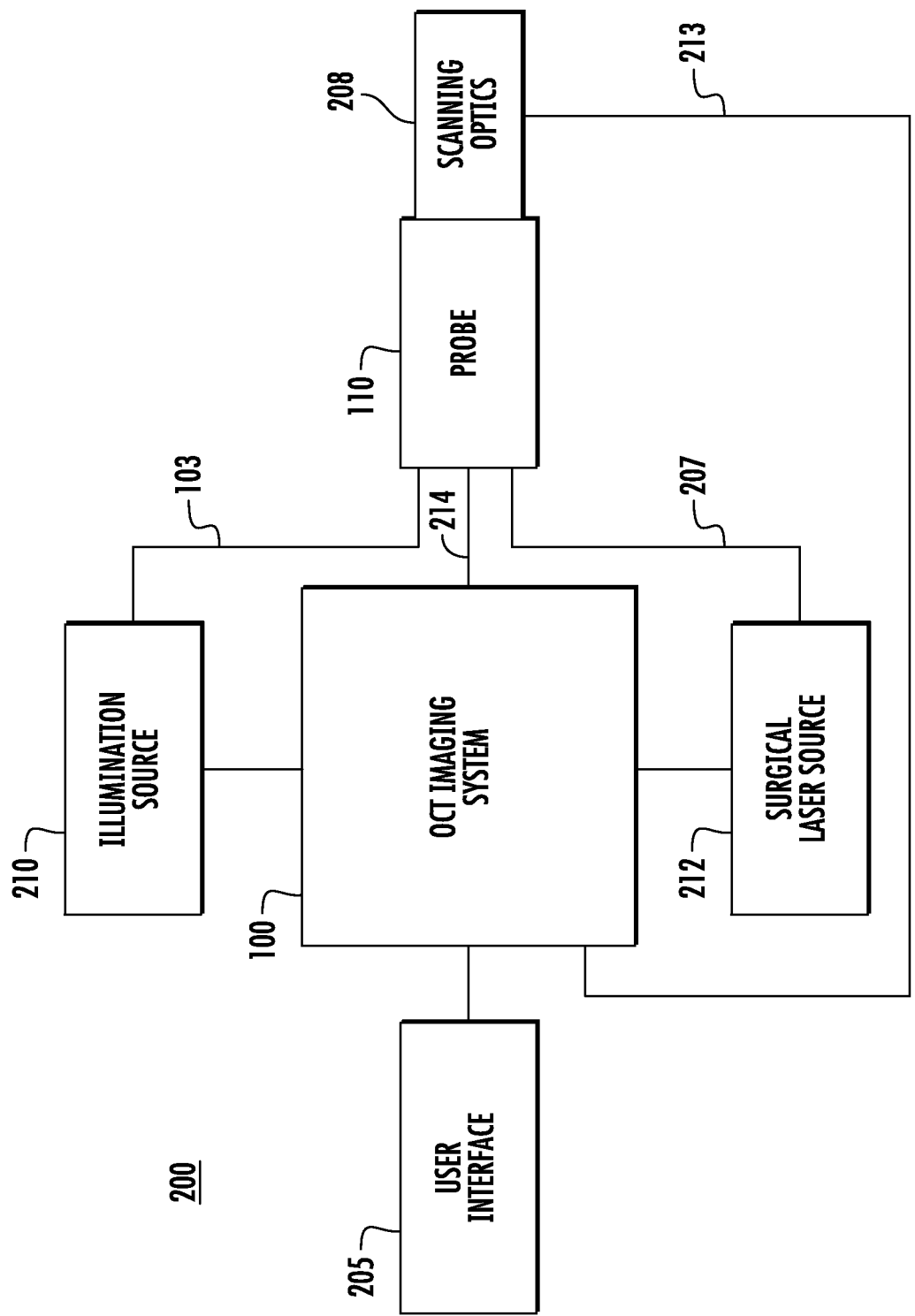
FIG. 2 illustrates a block diagram of an example laser surgical system according to aspects of the present disclosure.

FIG. 2 illustrates a laser surgical system 200, consistent with some embodiments of the disclosure. The laser surgery system 200 can include a surgical laser source 212 and the OCT imaging system 100. The surgical laser source 212 can guide a surgical beam 207 into an optical cable, which may be a fiber. The OCT imaging system 100 can guide a reference beam 214 into a second optical cable. The illumination source 210 can include an OCT light beam 103 guided into a third optical cable. In other embodiments, the surgical beam 207, the reference beam 214, and the OCT light beam 103 are guided into the same optical cable.

In some embodiments, the OCT imaging system 100 can be configured to create a one-dimensional image of a depth segment or depth region of the target at individual imaging points by performing a so-called A-scan. In other embodiments, the OCT system 100 may scan the surgical beam 207 over a sequence of imaging points along a line by a scanner or scanning optics 208, resulting in a sequence of A-scans that can be assembled into a two-dimensional image called a B-scan. In each case, the probe 110 may include the scanning optics 208. The OCT imaging system 100 with scanning optics 208 may include a scan control line 213, connecting the scanning optics 208 to the OCT imaging system 100. The operation and adjustment of the laser surgical system 200 can be facilitated by a user interface 205 in some embodiments.

As shown, the laser surgical system 200 may include the illumination source 210 to provide visible illumination light to assist the surgeon during the surgery. The illumination source may be any one of numerous surgical illumination sources, such as a xenon lamp, a collection of light emitting diodes, a laser, or any other suitable light source for generating light falling within a visible light spectrum to illuminate a target.

Consistent with some embodiments, the surgical laser source 212 may provide one or more beams of laser light having sufficient energy, power or fluence to effect a modification of the targeted tissue, such as effecting a photocoagulation of a targeted retinal tissue. The laser surgical system 200 may include additional surgical laser sources such as laser sources for photocoagulation, trabeculectomy, or other surgical applications, guiding their laser beam into the optical cable 207 as well.

Figure 3:
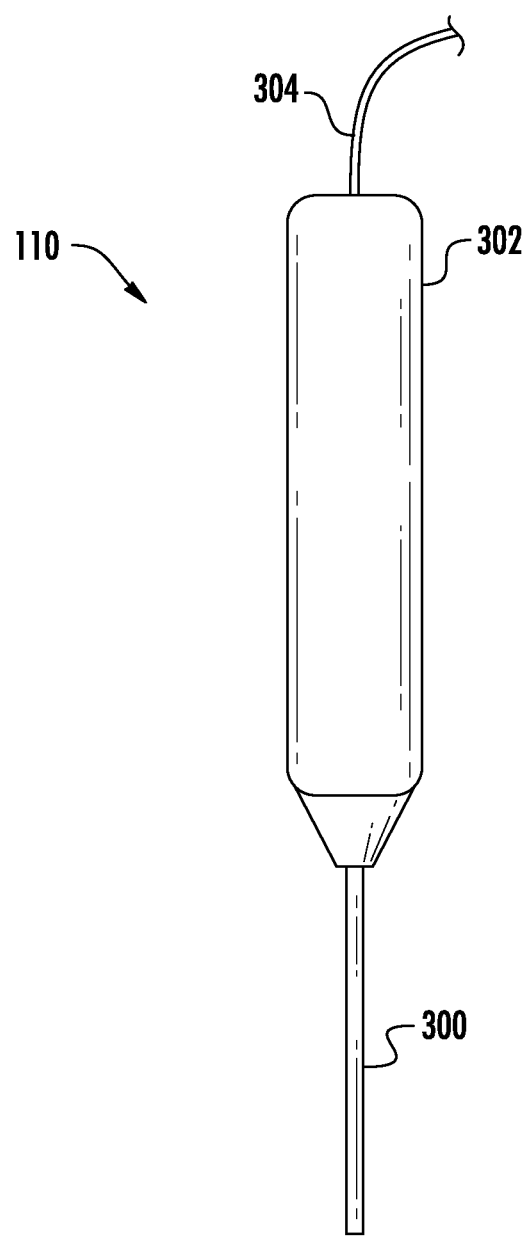
FIG. 3 is an illustration of an example probe of the OCT system according to aspects of the present disclosure.

FIG. 3 is a diagram illustrating a probe 110, consistent with some embodiments of the disclosure. As shown in FIG. 3, the probe 110 can include a cannula assembly 300 and a handpiece or housing 302. According to some embodiments, cannula assembly 300 may have an outer diameter of 300-700 microns, while handpiece or housing 302 may have a substantially larger diameter of 5-20 mm. The handpiece or housing 302 may be adapted for manual operation of the probe 110, or for robotic operation, to be held by an automated device that can be remotely operated. The optical cable 304 may include light-guides, such as optical fibers, carrying light from the OCT imaging system 100 and from surgical laser source 212 (FIG. 2). In ophthalmic surgical applications, the probe 110 may be inserted into the ophthalmic target, such as an eye. The controlling regulatory protocols in many cases require that probe 110 be disposed of after a single use, making calibration an influential process step.

Figure 4:
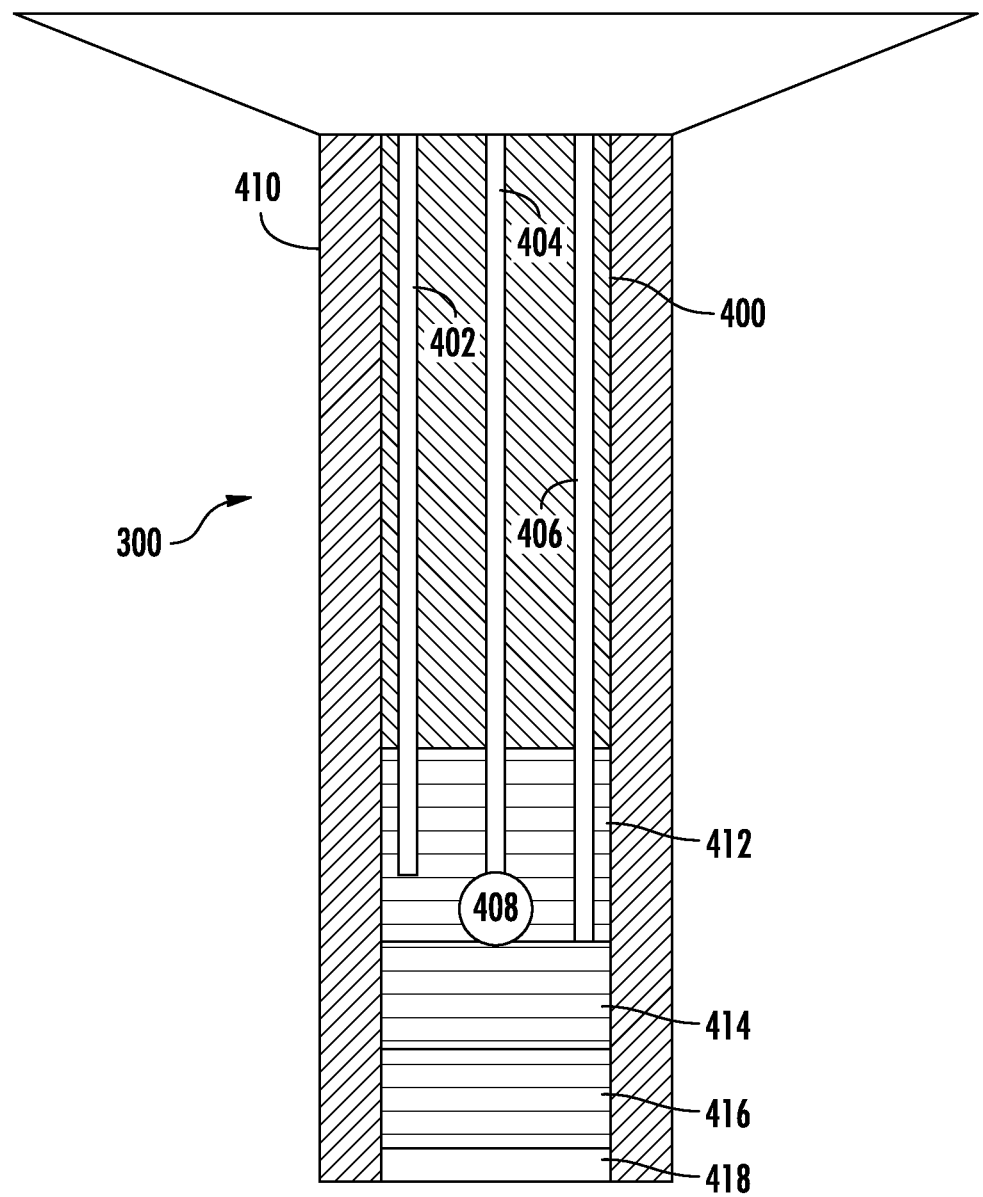
FIG. 4 is a block diagram of a cannula assembly according to aspects of the present disclosure.

FIG. 4 is a diagram illustrating an embodiment of cannula assembly 300 for the probe 110. The cannula assembly 300 may include a fiber bundle 400 that includes an OCT imaging fiber 402, a surgical laser fiber 404, and an illumination fiber 406. Consistent with some embodiments, the OCT imaging fiber 402 can be coupled to the OCT imaging system 100, the surgical laser fiber 404 can be coupled to the surgical laser source 212, and the illumination fiber 406 can be coupled to the illumination source 210, all via one or more optical cables. Optionally, consistent with some embodiments, the surgical laser fiber 404 may be coupled to a ball-lens multi-spot generator 408, which generates multiple spots on a target from the surgical beam transmitted through the surgical laser fiber 404. Although a ball-lens multi-spot generator 408 is shown in FIG. 4, in other embodiments, the fiber bundle 400 may include multiple surgical laser fibers instead of the ball lens 408 for generating multiple spots. In yet other embodiments, the cannula assembly 300 may not include the multi-spot generator 408.

Consistent with some embodiments, the OCT imaging fiber 402 can be a multimode fiber, a fiber bundle, a waveguide, or otherwise may be configured to transmit the reference beam 116 to a target and the returned reference beam, reflected from the target, for detection and processing. For example, in some embodiments, the OCT imaging fiber 402 may be a fiber assembly including fibers for the sample arm waveguide 108 and/or the reference arm waveguide 106. The cannula assembly 300 can also include a cannula tube 410 that surrounds fiber bundle 400 and other components of cannula assembly 300. In embodiments that include the scanning optics 208, the cannula tube 410 may include two counter-rotating cannulae to carry out the scanning of the reference beam 116.

Cannula assembly 300 may include a collimating and/or focusing lens 412. Consistent with some embodiments, the lens 412 can focus the beams emitted from the OCT imaging fiber 402 and from the surgical laser fiber 404 to the same plane so that the reference beam 116 can closely track the surgical beam 207. In embodiments with the scanning optics 208, the cannula assembly 300 can include scanner elements 414 and 416, and a fixed plate 418. The scanner elements 414 and 416 may be gradient index (GRIN) lenses. The scanner elements 414 and 416 can scan the reference beam 214, the surgical beam 207, and the OCT light beam 103, along lines or circles.

As described earlier, the imaging depth, the performance, and the high resolution of OCT imaging system 100 depends on calibration, which may include matching the optical path length of the reference arm waveguide 106 with the optical path length to the target, placed at a working distance from the end of probe 110, through the sample arm waveguide 108 and the probe 110. Since the probe 110 is disposable, before every procedure a new probe is coupled to the sample arm waveguide 108. Each probe 110 may be slightly different, thus the depth-calibration is shifted and the resolution of the OCT imaging system 100 is reduced after the installation of each new probe 110. This undermines the surgeon's ability to aim the surgical beam to its intended depth, as well as lowers the image quality, making the diagnostics of the ophthalmic tissue harder.

Figure 5:
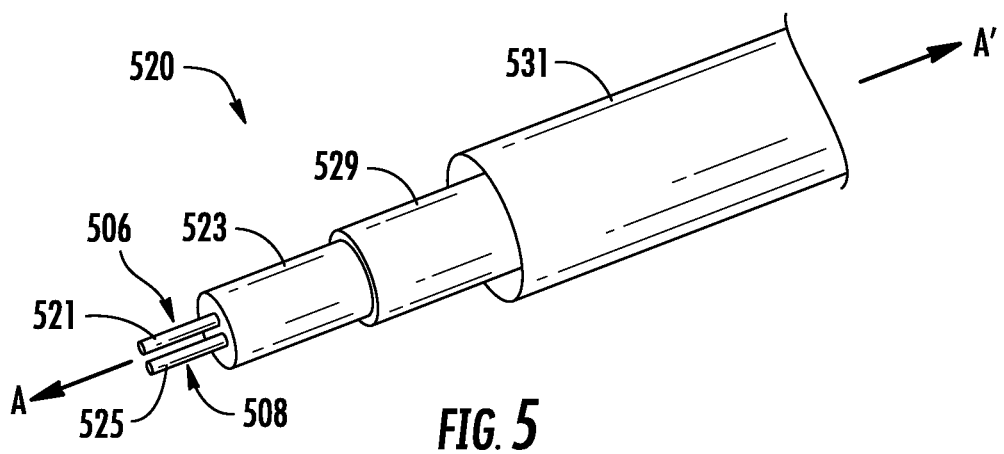
FIG. 5 is a perspective view of an example OCT fiber assembly according to aspects of the present disclosure.
Figure 6:
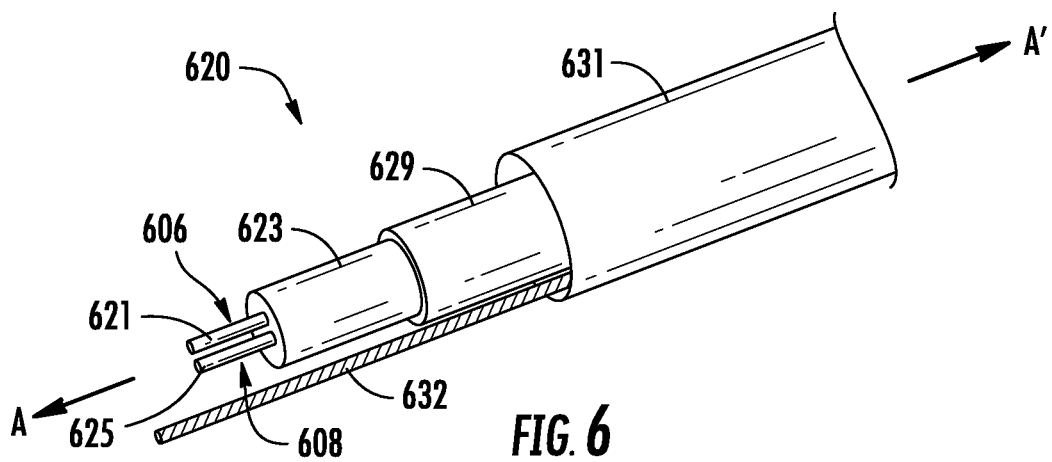
FIG. 6 is a perspective view of an example OCT fiber assembly according to aspects of the present disclosure.
Figure 7:
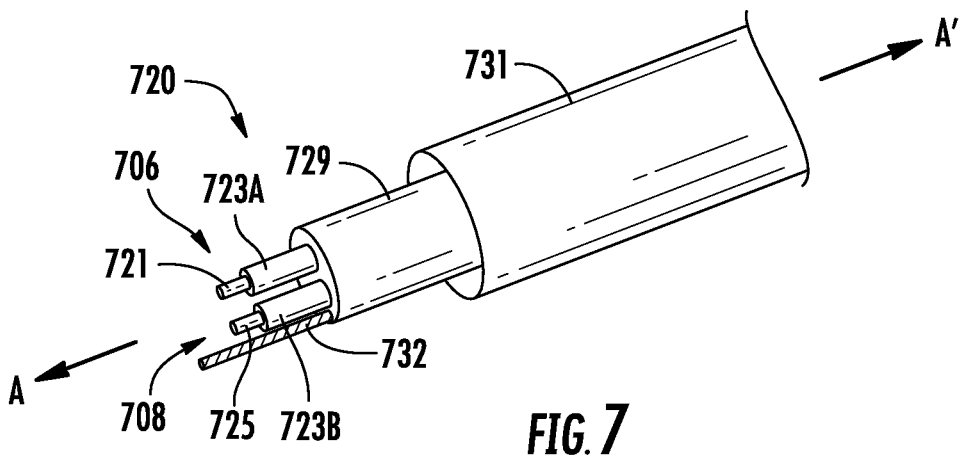
FIG. 7 is a perspective view of an example OCT fiber assembly according to aspects of the present disclosure.

Therefore, the performance of the OCT imaging system 100 can be improved by including a cladding, which couples the reference and sample fibers together. Fixing the reference arm waveguide 106 with the sample arm waveguide 108 avoids the process of re-calibration, for example, in the event of fiber stretching or movement. Turning now to FIGS. 5-7, various embodiments of an OCT fiber assembly according to the present disclosure will be described in greater detail. As first shown in FIG. 5, the fiber assembly 520 may include a reference arm waveguide 506 including a first core 521 surrounded by a cladding 523, and a sample arm waveguide 508 including a second core 525 also surrounded by the cladding 523. In some embodiments, the reference arm waveguide 506 and the sample arm waveguide 508 are initially the same length. The first core 521 and the cladding 523 together represent a fiber of the reference arm waveguide 506, while the second core 525 and the cladding 523 together represent a fiber of the sample arm waveguide 508. The first and second cores 521, 525 and the cladding 523 may be glass or a polymer. As shown, the cladding 523 may conform to an exterior surface of each of the first and second cores 521, 525. The cladding 523 physically/mechanically couples first and second cores 521, 525 together to improve calibration of a generated OCT image (e.g., OCT image 122 of FIG. 1) by minimizing axial movement (e.g., stretching, slipping, or shifting along axis A-A') of the reference arm waveguide 506 and the sample arm waveguide 508 relative to one another. In the event the reference arm waveguide 506 and/or the sample arm waveguide 508 are stretched or shift during use, both the reference arm waveguide 506 and the sample arm waveguide 508 may move together by an equal amount due to the cladding 523.

In some embodiments, the first and second cores 521, 525 may be cabled (e.g., twisted), in a right or left handed lay. Alternatively, the first and second cores 521, 525 may extend longitudinally along the cladding 523 such that the longitudinal axis (i.e., axis A-A') of the cladding 523 is parallel, or substantially parallel, to the first and second cores 521, 525. In some embodiments, to be considered parallel or substantially parallel, the first and second cores 521, 525 can include a small number of twists along the length of the fiber assembly 520. In one example, the first and second cores 521, 525 may have less than three (3) twists along the length of the fiber assembly 520 to be considered parallel or substantially parallel. In another example, the first and second cores 521, 525 may have one (1) twist along the length of the cable assembly 1. In some examples, the first and second cores 521, 525 may have between 0.1-0.25 twists/ft.

In some embodiments, cabling the first and second cores 521, 525 is beneficial, for example, in phase-sensitive applications in which the fiber assembly 520 is bent. In some cases, parallel waveguides might experience different stretching/compression if the fiber assembly 520 is bent. Twisting the first and second cores 521, 525 applies equivalent physical stretching/compression on the two waveguides, and maintains an even smaller difference in path length, which is beneficial for phase applications. In some embodiments, a substantial number of twists may be provided, for example, greater than 10 along the bend.

As further shown, the OCT fiber assembly 520 may further include a coating or buffer 529 formed over the cladding 523. In some embodiments, the buffer 529 may be a polymer, and may be conformally disposed over the cladding 523. The buffer 529 beneficially prevents the first and second cores 521, 525 from breaking when bent. A radial thickness of the buffer 529 can be selected as desired depending on the application and potential bend radius of the OCT fiber assembly 520. The buffer 529 provides further coupling of the first and second cores 521, 525 to minimize axial movement (e.g., along axis A-A') of the reference arm waveguide 506 and the sample arm waveguide 508 relative to one another.

The OCT fiber assembly 520 may further include a hollow jacket 531 disposed over the buffer 529. The hollow jacket 531 may be disposed along the length of the OCT fiber assembly 520 and may be made from a stretchable material (e.g., a polymer) or a relatively non-stretchable material (e.g., stainless steel).

As shown in FIG. 6, a fiber assembly 620 may include a reference arm waveguide 606 including a first core 621 surrounded by a cladding 623, and a sample arm waveguide 608 including a second core 625 also surrounded by the cladding 623. In some embodiments, the first core 621 and the cladding 623 together represent a fiber of the reference arm waveguide 606, while the second core 625 and the cladding 623 together represent a fiber of the sample arm waveguide 608. As shown, the cladding 623 may conform to an exterior surface of each of the first and second cores 621, 625. The cladding 623 is advantageously provided to improve calibration of a generated OCT image (e.g., OCT image 122 of FIG. 1) by fixing the reference arm waveguide 606 and the sample arm waveguide 608 to one another. For example, in the event the reference arm waveguide 606 and/or the sample arm waveguide 608 are stretched during use, both the reference arm waveguide 606 and the sample arm waveguide 608 are configured to be stretched by an equal, or a substantially equal, amount by the cladding 623.

In some embodiments, the first and second cores 621, 625 may be cabled (e.g., twisted), in a right or left handed lay. Alternatively, the first and second cores 621, 625 may extend longitudinally along the cladding 623 such that the longitudinal axis (i.e., axis A-A') of the cladding 623 is parallel, or substantially parallel, to the first and second cores 621, 625.

As further shown, the OCT fiber assembly 620 may further include a coating or buffer 629 formed over the cladding 623. The buffer 629 provides further coupling of the first and second cores 621, 625 to minimize axial movement (e.g., along axis A-A') of the reference arm waveguide 606 and the sample arm waveguide 608 relative to one another.

The OCT fiber assembly 620 may further include a hollow jacket 631 disposed over the buffer 629. The hollow jacket 631 may be disposed along the length of the OCT fiber assembly 620 and may be made from a stretchable material (e.g., a polymer) or a relatively non-stretchable material (e.g., stainless steel).

In this embodiment, the OCT fiber assembly 620 may further include a non-stretchable wire 632 extending into the hollow jacket 631. In some embodiments, the non-stretchable wire 632 extends along the cladding 623, parallel or substantially parallel to the first and second cores 621, 625. The non-stretchable wire 632 may be positioned between an exterior surface of the buffer 629 and an interior surface of the hallow jacket 631, and is provided to minimize or eliminate the stretching of the first and/or second cores 621, 625 as the non-stretchable wire 632 is restrained on both ends of the OCT fiber assembly 620. Although not shown, the non-stretchable wire 632 may be clamped or secured on each end by a fastener or housing, which may be a metal or a polymer. In some embodiments, the non-stretchable wire 632 may be a polymer, which minimizes thermal stretching, or a metallic wire, which minimizes substantial mechanical stretching.

As shown in FIG. 7, a fiber assembly 720 may include a reference arm waveguide 706 including a first core 721 surrounded by a first section of cladding 723A, and a sample arm waveguide 708 including a second core 725 surrounded by second section of cladding 723B. In some embodiments, the first core 721 and the first section of cladding 723A together represent a fiber of the reference arm waveguide 706, while the second core 725 and the second section of cladding 723B together represent a fiber of the sample arm waveguide 708. As shown, the first section of cladding 723A may concentrically conform to an exterior surface of the first core 721, while the second section of cladding 723B may concentrically conform to an exterior surface of the second core 725.

As shown, the first section of cladding 723A and the second section of cladding 723B are positioned separate from one another, but coupled together by a coating or buffer 729 formed over the first and second sections of cladding 723A-B. In this way, the coating or buffer 729 serves as the cladding that couples the reference arm waveguide 706 and the sample arm waveguide 708. The buffer 729 improves calibration of a generated OCT image (e.g., OCT image 122 of FIG. 1) by reducing or eliminating axial movement (e.g., along axis A-A') of the reference arm waveguide 706 and the sample arm waveguide 708 relative to one another. For example, in the event the reference arm waveguide 706 and/or the sample arm waveguide 708 are stretched during use, both the reference arm waveguide 706 and the sample arm waveguide 708 will move together, thus causing the relative lengths of the reference arm waveguide 706 and the sample arm waveguide 708 to remain the same.

In some embodiments, the reference arm waveguide 706 and the sample arm waveguide 708 may be cabled (e.g., twisted), in a right or left handed lay. Alternatively, the reference arm waveguide 706 and the sample arm waveguide 708 may extend longitudinally along the buffer 729 such that the longitudinal axis (i.e., axis A-A') of the buffer 729 is parallel, or substantially parallel, to the reference arm waveguide 706 and the sample arm waveguide 708.

The OCT fiber assembly 720 may further include a hollow jacket 731 disposed over the buffer 729. The hollow jacket 731 may be disposed along the length of the OCT fiber assembly 720 and may be made from a stretchable material (e.g., a polymer) or a relatively non-stretchable material (e.g., stainless steel).

In this embodiment, the OCT fiber assembly 720 may further include a non-stretchable wire 732 extending into the buffer 729. In other embodiments, the non-stretchable wire 732 is not surrounded by the buffer 729. As shown, the non-stretchable wire 732 is circumferentially surrounded by the buffer 729 at least partially along a length of the non-stretchable wire 732. In some embodiments, the non-stretchable wire 732 extends parallel, or substantially parallel, to the reference arm waveguide 706 and the sample arm waveguide 708.

In sum, the OCT imaging system and the OCT fiber assembly described herein advantageously prevent asymmetrical stretching or shifting of reference and sample fibers by mechanically/physically coupling the reference and sample fibers together using a cladding. As a result, if either fiber is stretched or moved, both fibers are stretched or moved together, and the OCT calibration remains valid. Stated another way, the resulting reconstructed OCT image does not shift due to difference in fiber path lengths.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, as used herein, an element or operation recited in the singular and proceeded with the word "a" or "an" should be understood as not excluding plural elements or operations, unless such exclusion is explicitly recited. Furthermore, references to "one approach" or "one embodiment" of the present disclosure are not intended to be interpreted as excluding the existence of additional approaches that also incorporate the recited features.

Still furthermore, spatially relative terms, such as "beneath," "below," "lower," "central," "above," "upper," "over" and the like, may be used herein for ease of describing one element's relationship to another element(s) as illustrated in the figures. It will be understood that the spatially relative terms may encompass different orientations of the device in use or operation in addition to the orientation depicted in the figures.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An Optical Coherence Tomography (OCT) imaging system, comprising:
    an OCT light source operable to emit an OCT light beam;
    a beam splitter operable to split the OCT light beam into a sample beam, transferred to a sample arm waveguide, and a reference beam, transferred to a reference arm waveguide, wherein the reference arm waveguide comprises a first core surrounded by a first section of cladding concentrically disposed over the first core, and wherein the sample arm waveguide comprises a second core surrounded by a second section of cladding concentrically disposed over the second core, wherein the first section of cladding and the second section of cladding improves a calibration of a generated OCT image by reducing axial movement of the sample arm waveguide and reference arm waveguide relative to one another;
    a buffer disposed over the first section of cladding and the second section of cladding, wherein the first section of cladding and the reference arm waveguide and the second section of cladding and the sample arm waveguide and are twisted within the buffer such that there exists substantially equivalent physical stretching and/or compression on the reference arm waveguide and the sample arm waveguide.

2. The OCT imaging system of claim 1, further comprising a probe operable to guide the sample beam onto a target and to receive a returned sample beam from the target.

3. The OCT imaging system of claim 2, further comprising an imaging processor operable to generate the OCT image from an interference beam detected by an imaging detector.

4. The OCT imaging system of claim 3, wherein the beam splitter is operable to generate the interference beam from the returned sample beam and a returned reference beam.

5. The OCT imaging system of claim 1, wherein the reference arm waveguide comprises a first core surrounded by the cladding, and wherein and the sample arm waveguide comprises a second core surrounded by the cladding.

6. The OCT imaging system of claim 1, further comprising a hollow jacket disposed over the buffer.

7. The OCT imaging system of claim 1, wherein the buffer is disposed over the first section of cladding and the second section of cladding.

8. The OCT imaging system of claim 1, further comprising a non-stretchable wire extending substantially parallel along the reference arm waveguide and the sample arm waveguide.

9. An Optical Coherence Tomography (OCT) fiber assembly, comprising:
    a reference arm waveguide receiving a reference beam, wherein the reference arm waveguide comprises a first core surrounded by a first section of cladding concentrically disposed over the first core;
    a sample arm waveguide receiving a sample beam, wherein the sample arm waveguide comprises a second core surrounded by a second section of cladding concentrically disposed over the second core;
    wherein the first section of cladding and the second section of cladding improves a calibration of a generated OCT image by minimizing axial movement of the sample arm waveguide and reference arm waveguide relative to one another; and
    a buffer disposed over the first section of cladding and the second section of cladding, wherein the first section of cladding and the reference arm waveguide and the second section of cladding and the sample arm waveguide and are twisted within the buffer such that there exists substantially equivalent physical stretching and/or compression on the reference arm waveguide and the sample arm waveguide.

10. The OCT fiber assembly of claim 9, wherein the reference arm waveguide and the sample arm waveguide are glass, and wherein the buffer is a polymer.

11. The OCT fiber assembly of claim 9, further comprising a hollow jacket disposed over the cladding.

12. The OCT fiber assembly of claim 9, wherein the cladding conforms to an exterior surface of both the first and second cores.

* * * * *